(12) United States Patent
Vollenbroich et al.

(10) Patent No.: US 6,787,520 B2
(45) Date of Patent: Sep. 7, 2004

(54) INACTIVATING PROCESS FOR LIPID ENVELOPPED VIRUS, AND NEW ANTIVIRUS LIPOPEPTIDES

(76) Inventors: Dirk Vollenbroich, Allerstrasse 6, 12049 Berlin (DE); Joachim Vater, Nibelungenstrasse 14c, 14109 Berlin (DE); Georg Pauli, Lutzowstrasse 51f, 10785 Berlin (DE); Roza Maria Kamp, Knesebeckstrasse 9a, 14167 Berlin (DE)

( * ) Notice: Subject to any disclaimer, the term of this patent is extended or adjusted under 35 U.S.C. 154(b) by 0 days.

(21) Appl. No.: 09/242,343

(22) PCT Filed: Aug. 11, 1997

(86) PCT No.: PCT/EP97/04353

§ 371 (c)(1),
(2), (4) Date: Apr. 12, 1999

(87) PCT Pub. No.: WO98/06744

PCT Pub. Date: Feb. 19, 1998

(65) Prior Publication Data

US 2002/0187929 A1 Dec. 12, 2002

(30) Foreign Application Priority Data

Aug. 12, 1996 (DE) .......................... 196 33 684

(51) Int. Cl.$^7$ ...................... A61K 38/00; A61K 38/08; A61K 38/12; C07K 4/02; C07K 4/04
(52) U.S. Cl. ..................... 514/9; 514/2; 514/11; 514/16; 530/300
(58) Field of Search ................. 514/2, 7, 8, 9, 514/11, 16; 544/176, 277, 280, 310; 424/78.07; 530/300, 317, 322, 323, 329, 341

(56) References Cited

U.S. PATENT DOCUMENTS

| 4,591,505 A | 5/1986 | Prince |
| 4,613,501 A | 9/1986 | Horowitz |
| 4,841,023 A | 6/1989 | Horowitz |
| 6,114,108 A | * 9/2000 | Budowsky ...................... 435/2 |

FOREIGN PATENT DOCUMENTS

| DE | A 195 21938 | 12/1996 |
| EP | 050061 | 4/1982 |
| EP | 761682 A1 | 3/1997 |
| WO | 9 532990 | 12/1995 |
| WO | WO 9806744 | 2/1998 |

OTHER PUBLICATIONS

Weislow et al., Journal of the National Cancer Institute, Voume 81, pp. 577–586 91989).*
Webster's II New Riverside Dictionary, The Riverside Publishing Company, Boston, p. 976, 1994.*
Wagner et al., Transfusion Medicine Reviews, vol. V, No. 1:18–32, Jan. 1991.*
Vollenbroich et al., Applied and Environmental Microbiology, 63(1):44–49, 1997.*
Vater et al.m proc. 4th European Congress on Biotechnology, 3:266–269, 1987.*
N. Naruse et al, Journal of Antibiotics, vol. 43, No. 3, Mar. 1990, pp. 267–280.
H. Itokawa et al, Chemical and Pharmaceutical Bulletin, vol. 42, No. 3, Mar. 1994, pp. 604–607.
B. Horowitz et al, Vox Sanguinis, vol. 54, No. 1, 1988, pp. 14–20.
H. Rabenau et al., "Die Infektionssicherheit biotechnologischer Pharmazeutika aus virologischer Sicht", *GIT Verlag GmbH*, pp. 58–59, (1990).
B. Horowitz et al., *Transfusion*, 25(6): pp. 516–522, (1985).
B. Horowitz et al., *Transfusion*, 25(6): pp. 523–527, (1985).
W. Stephan, *Morgenthaler*, 56: pp. 122–127 (1989).
T. Nowak et al., *Biologicals*, 20: pp. 83–85 (1992).
D. Piszkiewicz et al., *Morgenthaler*, 56: pp. 44–54 (1989).
F. Baumgart et al., *Biochemical and Biophysical Research Communications*, 177 (3): pp. 998–1005 (1991).
L. Cavalli–Sforza, *Biometrie Grundzuge biologisch–medizinischer Statistik*, (Gustav Fischer Verlag, Stuttgart) pp. 170–173.
Tim Mosmann, *Journal of Immunological Methods*, 65: pp. 55–63, (1983).
Flick and Gifford, *J. Immunol. Meth.* 68: pp. 167–175 (1984).

* cited by examiner

Primary Examiner—James Housel
Assistant Examiner—Zachariah Lucas
(74) Attorney, Agent, or Firm—Birch, Stewart, Kolasch & Birch, LLP.

(57) ABSTRACT

The invention relates to an extraordinarily efficient method of inactivating lipid-enveloped viruses, such as herpes or retroviruses, in biological or biotechnological—particularly pharmaceutical—products, as well as in cell cultures by adding a cyclic lipopeptide or a mixture of lipopeptides or salts or esters thereof at specific concentrations. Lipopeptides were found to have a surprisingly high inactivation potential for lipid-enveloped viruses and in addition, they offer the advantage of an exceedingly low in vivo toxicity, so that the step of removing the inactivating agent from pharmaceutical products or cell cultures can be omitted. The invention is also directed to new antiviral lipopeptides which belong to the surfactins.

14 Claims, No Drawings

INACTIVATING PROCESS FOR LIPID ENVELOPPED VIRUS, AND NEW ANTIVIRUS LIPOPEPTIDES

This application is the national phase under 35 U.S.C. §371 of prior PCT International Application No. PCT/EP97/04353 which has an International filing date of Aug. 11, 1997 which designated the United States of America.

The invention relates to an extraordinarily efficient method of inactivating lipid-enveloped viruses such as herpes or retroviruses in biological or biotechnological—particularly pharmaceutical—products, as well as in cell cultures by adding a cyclic lipopeptide or a mixture of lipopeptides or salts or esters thereof at specific concentrations. Lipopeptides were found to have a surprisingly high inactivation potential for lipid-enveloped viruses and in addition, they offer the advantage of an exceedingly low in vivo toxicity, so that the step of removing the inactivating agent from pharmaceutical products or cell cultures can be omitted. The invention is also directed to new antiviral lipopeptides which belong to the surfactins.

At the latest, the AIDS epidemic has brought the realization into the mind of the general public that not only HI viruses but rather, a variety of agents pathogenic for humans may be transmitted, for example, via blood transfusions, pharmaceuticals, transplantations, etc.. In general, it is obligatory today that each pharmaceutical agent prepared from biological material or having come in contact with same is rated as potentially contaminated by microbes or viruses, and that infection-related safety is verified. As a result of the development of molecular-biological methods for manufacturing pharmaceutical agents, the risk of infection by various microbial contaminants has increased further. Animal or human cell lines are frequently used in the biotechnological production of pharmaceuticals. In these cells, in particular, virus infections by endogenous viruses, latent virus infections, or contaminations cannot be excluded completely. The infection-related safety of biotechnological pharmaceuticals, e.g., vaccines, monoclonal antibodies, hormones, or recombinant proteins therefore necessitates removal of any infectious, undesirable particles, which, in principle, may be associated with a considerable loss of research time and means, or productivity. Virus safety of blood and blood products can only be guaranteed by testing and selecting the blood donations, in combination with evaluating and prophylactically using efficient and reliable methods of virus inactivation and elimination.

To inactivate and eliminate viruses from pharmaceutical products, various methods are employed alone or in combination. Chromatographic methods, pH shift, extraction, and fractionation using various organic solvents, salt precipitation, heat treatment, and filtration techniques are employed in case of structurally simple and stable products [Rabenau & Doerr (1990), "Die Infektionssicherheit biotechnologischer Pharmazeutika aus virologischer Sicht", p. 58, GIT VERLAG GmbH, Darmstadt]. Where sensitive or complex biological materials are involved, substances having an antiviral effect are frequently used. Inter alia, the following methods are employed:

the combined use of solvents (e.g., extraction with ether) and synthetic detergents (e.g., Triton X-100) [B. Horowitz et al. (1985), Transfusion 25, 516–522];

the use of β-propiolactone in combination with UV light, as well as methylene blue in combination with photoactivation [W. Stephan (1989) pp. 122–127, in J.-J. Morgenthaler (Ed.); Virus Inactivation in Plasma Products; Curr. Stud. Hematol. Blood Transfus. No. 56, Karger, Basel];

pasteurization of liquid material [T. Nowak (1992), Biologicals 20, 83–85];

heating of lyophilized material [D. Piszkiewicz et al. (1989), pp. 44–54, in J.-J. Morgenthaler (Ed.), Virus Inactivation in Plasma Products., Curr. Stud. Hematol. Blood Transfus. No. 56, Karger, Basel];

irradiation with gamma rays (e.g., cobalt-60) [B. Horowitz et al. (1988), Transfusion 25, 523–527].

The literature describes a number of virus inactivation methods for blood products, particularly human blood plasma. Thus, in U.S. Pat. No. 4,591,505, A. M. Prince discloses an inactivation method for hepatitis B virus wherein the blood products are added with alcohol and either a non-ionic detergent or an ether or a mixture of both as virus-inactivating agent. Polyoxyethylene derivatives or sulfobetains are used as non-ionic detergents.

In U.S. Pat. No. 4,841,023 and in Vox-Sang. 54, 14–20 (1988), S. Karger A G, Basel, B. Horowitz describes the inactivation of lipid-containing viruses in blood products by fatty acids, and in U.S. Pat. No. 4,613,501 by $C_1$–$C_4$ alkyl oleic acid.

In EP 0,050,061 E. Shanbrom discloses a method of reducing undesirable effects such as pyrogenicity, hepatitis infectiousness, and aggregation in biological and pharmaceutical products, particularly blood products as well, using a treatment with non-denaturing amphiphilics such as non-ionic surfactants (e.g., Tween 80).

The inactivation and elimination of viruses from cell cultures is effected using antiviral substances which normally inhibit virus replication.

None of the inactivation methods used up to now can safely inactivate or eliminate all viruses which may occur in biological material. Methods such as pasteurization or heat treatment normally require the use of stabilizers, and in addition, there is the problem of protein denaturation. To date, the use of solvents and synthetic surfactants considered as suitable for inactivating lipid-enveloped viruses could not be assessed as entirely safe due to deviating results in inactivation kinetics or lacking systematic investigations as a result of high toxicity of the substances in cell cultures. Owing to their structure or stability, a variety of biotechnological products cannot be subjected to expensive purification or inactivation using product-damaging or cytotoxic antiviral substances such as solvents.

It was therefore the object of the invention to provide a mild method of inactivating lipid-enveloped viruses in biological or biotechnological products and cell cultures, which method enables to render these products or cell cultures free of viruses in an exceedingly rapid and effective fashion, with no denaturing of products or impairing the cell cultures in their productivity. Also, said method should allow the treatment of heat-labile products and avoid substances having in vivo toxicity.

The object of the invention is accomplished by using cyclic peptides containing β-hydroxyfatty acids and β-aminofatty acids (lipopeptides). These lipopeptides were found to have a surprisingly high inactivation potential for lipid-enveloped viruses, and thus, they are excellent for use in accomplishing the object of the invention. Part of these lipopeptides were found to be substantially more effective compared to synthetic surfactants used in virus inactivation up to now. In addition, they readily undergo biological degradation and have a substantially lower in vivo toxicity than synthetic surfactants. Compared to conventional antiviral substances, the lipopeptides used according to the invention have the advantage of thermal stability and good water-solubility.

From the literature, two [Ile$^7$] and [Leu$^7$] surfactins which belong to the lipopeptides, are known to exhibit moderate anti-HIV-1 activity (H. Itokawa et al., Chem. Pharm. Bull. 42, 604–607 (1994)). In Journal of Antibiotics, Japan XLIII 267–280 (1989), N. Naruse et al. describe pumilacidins as antivirally effective against herpes simplex virus (HSV-1). Neither of these papers indicates the considerable inactivation potential of these substances, allowing extensive inactivation of lipid-enveloped viruses at low concentrations within an exceedingly short time.

Thus, the inactivation method according to the invention is characterized in that the biological or biotechnological products are added with a lipopeptide or a salt or ester thereof, or a mixture of lipopeptides or salts or esters thereof at an overall concentration of 1–100 μM, preferably 1–80 μM, and that the inactivation is performed at room temperature within from 30 min to 2 hours at maximum, with about 99% of the viruses already being inactivated after 30 min. As a result of the exceedingly low in vivo toxicity of the lipopeptides used according to the invention, these inactivating substances may also be allowed to remain in the pharmaceutical products at the above-mentioned concentrations. Following inactivation, the lipopeptides employed may also be removed from the products by reversed phase HPLC on a $C_{18}$ column, or by adsorption chromatography on a silica gel column.

As the lipopeptides employed according to the invention are thermally stable, the inactivation process may also be performed at elevated temperatures, preferably at 30–60° C., depending on the thermal stability of the products to be treated. The inactivation efficiency was found to have a linear temperature dependence. Thus, a temperature increase of about 10° C. already results in an increase of the inactivation rate by a factor of about 2.4, so that virus inactivation is possible even within 5–30 min at 30–60° C. at and the above-mentioned concentrations. In general, the viruses may also be inactivated at temperatures as low as 0° C. Depending on the particular species, however, this may take longer than 2 hours.

According to the invention, the virus inactivation in cell cultures is characterized in that the serum-free culture medium is added with a lipopeptide or a salt or ester thereof, or a mixture of lipopeptides or salts or esters thereof at an overall concentration of 1–65 μM, preferably 1–50 μM. When using a culture medium containing serum up to 5 vol.-%, e.g., FCS, the lipopeptide concentration required for complete inactivation is 10–100 μM, preferably 30–90 μM.

The inactivation process of the invention may be carried out within a broad pH range of 4–9, preferably 5.5–8.

Naturally occurring, chemically synthesized cyclic lipopeptides, as well as those produced and modified by genetic engineering may be used in the inactivation process of the invention.

The cyclic lipopeptides used according to the invention can readily be prepared according to previously described methods well-known to those skilled in the art. The *Bacillus subtilis* microorganism, among others, forms numerous lipopeptides in vivo which undergo secretion into the surrounding medium at high concentrations, from which they may be isolated.

Predominantly, viruses which can be inactivated by means of the method of the invention are herpes viruses preferably HSV-1, HSV-2, BHV-1, SHV-1, immunodeficiency viruses, preferably HIV-1, HIV-2, $SIV_{agm}$, the vesicular stomatitis virus (VSV), and the Semliki-Forest virus (SFV). According to the invention, however, other lipid-enveloped viruses may also be inactivated effectively.

According to the invention, lipoheptapeptides of general formula I, $$C_{10\text{-}12}-\underset{\underset{O-L-\underset{7}{Y}-D-\underset{6}{Leu}-L-\underset{5}{Asp}-L-\underset{4}{Z}}{|}}{CHCH_2CO}-L-\underset{1}{Glu}-L-\underset{2}{X}-D-\underset{3}{Leu} \quad (I)$$

also referred to as surfactins, the salts, esters or mixtures thereof are preferably used in the inactivation, in which formula I X and Y represent the amino acids Leu, Ile or Val, Z represents the amino acids Val or Ala, and $C_{10\text{-}12}$ represents a linear or branched, saturated alkyl chain. According to the invention, the surfactins of general formula I, with X being Val or Ile, and the esters thereof are new compounds which are also subject of the present invention.

For example, the surfactin mixture produced by the strain *Bacillus subtilis* ATCC 21332 and the more productive strain *Bacillus subtilis* OKB 105 was found to be highly suitable in the virus inactivation according to the invention. The surfactin from these *Bacillus subtilis* strains is a mixture of isoforms, i.e., compounds of general formula I differing in the chain length of the fatty acid, the branching of the fatty acid, and the amino acids X, Y and Z, as illustrated above.

Individual compounds of general formula I, e.g., surfactin isoforms having a fatty acid residue of $C_{14}$ alkyl or $C_{15}$ alkyl (i.e., $C_{11}$ or $C_{12}$ alkyl in general formula I) which, for example, may be isolated from the surfactin mixture obtained by fermentation of the above-mentioned strains or synthesized by chemical means, likewise exhibit a high inactivation potential. Thus, it has been determined that, e.g., surfactins of general formula I having $C_{15}$ alkyl as fatty acid residue inactivate vesicular stomatitis virus (VSV) even more rapidly compared to the surfactin mixture. Surfactins having $C_{14}$ alkyl as fatty acid residue were found to be effective compounds in the inactivation of porcine herpes virus (SHV-1).

Pumilacidins of general formula I in the form of individual components or mixtures, such as described in Journal of Antibiotics, Japan XLIII 267–280 (1989), pp. 267–280, for example, as well as the salts or esters thereof may also be used according to the invention.

In one specific embodiment, compounds of general formula I wherein the amino acids Glu and/or Asp are esterified are employed in the process of the invention. The monoesters of the compounds of general formula I, wherein just one of the above-mentioned amino acids is esterified, exhibit quite specific effects. Thus, the $C_{14}$ alkyl monoester of general formula I, for example, was found to inactivate the porcine herpes virus within 20 minutes at a concentration of 40 μM by a factor of $<10^4$. The $C_{15}$ alkyl monoesters of general formula I were also capable of inactivating the Semliki-Forest virus (SFV) within 20 minutes at a concentration of 40 μM by a factor of $>10^4$. The inactivation of SFV using $C_{14}$ or $C_{15}$ alkyl monoesters is exemplified in Table 1 below:

TABLE 1

Inactivation of SFV

| Lipopeptide | Incubation period (min) | | | | | |
|---|---|---|---|---|---|---|
| | 0 | 1 | 5 | 10 | 15 | 20 |
| | Titer (TCID$_{50}$/ml) | | | | | |
| Monoester C$_{14}$ | 2.4 × 10$^4$ | 1.7 × 10$^3$ | 98.0 | 30.0 | 30.0 | 30.0 |
| Monoester C$_{15}$ | 2.5 × 10$^5$ | 173.0 | 99.0 | 25.0 | 10.0 | 6.5 |

In the meaning of the invention, biological products represent products isolated from mammals, such as blood products, products isolated from blood, such as vaccines and plasma derivatives. Biotechnological pharmaceutical products are understood to be active substances produced by biotechnological means, such as human proteins (hGH, TNF, t-PA, EPO), or coagulation factors (e.g., factor VIII); however, the invention is not limited to the above-mentioned products from cell cultures.

With reference to the embodiments, the invention will be illustrated in more detail below.

EXAMPLE 1
Preparation of Surfactins of General Formula I

The surfactin mixture used according to the invention, which contains the compounds of general formula I, is prepared by cultivating *Bacillus subtilis* strains, particularly *Bacillus subtilis* ATCC 21332 or *Bacillus subtilis* OKB 105, and purified as described in Biochemical and Biophysical Research Communications, Vol. 177, No. 3 (1991), pp. 998–1005.

EXAMPLE 2
Isolation of the Isoforms from the Surfactin Mixture Prepared According to Example 1

The individual compounds of general formula I were isolated by preparative RP HPLC on EnCa Pharm 100 RP 18-TS (5 µm, 250×16 mm) using an LKB HPLC system. The surfactin isoforms were eluted using acetonitrile gradients. Solvent A contained 40% acetonitrile and 60% 10 mM NH$_4$OAc (v/v), pH 6.9. Solvent B was 100% acetonitrile. Following lyophilization, the isoforms were obtained as a white powder and determined using NMR spectroscopy and MS spectrometry. The isolated compounds are shown in Table 2.

TABLE 2

Isolated isoforms
(In the following Table, the amino acid (AA) at position 4 is valine, and AA2 is leucine, unless otherwise stated)

| No. of fraction | Amino acids | Molecular mass in daltons | Fatty acid chain length |
|---|---|---|---|
| 1 | [Leu7]- | 1008 | C$_{13}$ |
| 2 | [Val7]- | 994 | C$_{13}$ |
| 3 | [Ile2, Val7]- | 994 | C$_{13}$ |
| 4 | [Leu7]- | 1022 | C$_{14}$ |
| | [Ile7]- | 1008 | C$_{13}$ |
| 5 | [Val7]- | 1008 | C$_{14}$ |
| 6 | [Ile2, Val7]- | 1008 | C$_{14}$ |
| 7 | [Leu7]- | 1036 | C$_{15}$ |
| 8 | [Ile7]- | 1022 | C$_{14}$ |
| 9 | [Val7]- | 1022 | C$_{15}$ |
| 10 | [Ile2, Val7]- | 1022 | C$_{15}$ |
| 11 | [Ile7]- | 1036 | C$_{15}$ |
| 12 | [Ile2, Ile7]- | 1036 | C$_{15}$ |

The fractions 3, 6, 10, and 12 are new compounds, [Ile2, Val7]-surfactin and [Ile2, Ile7]-surfactin, which have not been described up to now. The $^1$H-NMR data of the compounds in fractions 10 and 12 at 30° C. in pyridine-d$_5$ are illustrated below:

TABLE 3

| Amino acid | ppm NH | C$_\alpha$H | C$_\beta$H | C$_\gamma$H | C$_\delta$H |
|---|---|---|---|---|---|
| [Ile2, Val7] surfactin (fraction 10) | | | | | |
| L-Glu (1) | 8.84  5.16 | 2.68, | 2.51 | 2.88 | — |
| L-Ile (2) | 9.13  4.71 | | 2.23 | 1.70,  1.39 | 1.18 |
| D-Leu (3) | 9.23  5.04 | 2.08, | 1.87 | 1.87 | 0.93.  0.90 |
| L-Val (4) | 8.80  4.86 | | 2.61 | 1.18 | — |
| L-Asp (5) | 9.25  5.60 | 3.50, | 3.35 | — | — |
| D-Leu (6) | 8.72  5.20 | | 1.96 | 1.96 | 0.90 |
| L-Val (7) | 8.88  4.92 | | 2.50 | 1.12 | — |
| Fatty acid | $^3$H 5.50 | $^2$H 2.98, | 2.78  $^4$H 2.05, | 1.90 | $^n$H 1.41,  1.25 |
| [Ile2, Ile7] surfactin (fraction 12) | | | | | |
| L-Glu (1) | 8.80  5.17 | 2.67, | 2.57 | 2.91 | — |
| L-Ile (2) | 9.10  4.72 | | 2.24 | 1.70,  1.42 | 1.18 |
| D-Leu (3) | 9.25  5.04 | 2.07, | 1.86 | 1.86 | 0.93.  0.90 |
| L-Val (4) | 8.80  4.86 | | 2.63 | 1.19 | — |
| L-Asp (5) | 9.25  5.63 | 3.51, | 3.38 | — | — |
| D-Leu (6) | 8.75  5.20 | | 1.97 | 1.97 | 0.92 |

TABLE 3-continued

| Amino acid | ppm | NH | $C_\alpha H$ | $C_\beta H$ | | $C_\gamma H$ | $C_\delta H$ | |
|---|---|---|---|---|---|---|---|---|
| L-Ile (7) | 8.84 | 4.96 | 2.22 | 1.70, | | 1.41 | 1.12 | |
| Fatty acid | | $^3$H 5.50 | $^2$H 3.00, | 2.79 | $^4$H 2.06, | 1.92 | $^n$H 1.43, | 1.27 |

EXAMPLE 3
Preparation of Monomethyl Esters of the Compounds of General Formula I An esterification of the surfactin mixture obtained in Example 1 was carried out using methanol/HCl, and the individual monomethyl esters were isolated. To prepare the monomethyl esters, 100 mg of surfactin mixture was incubated with 50 ml of methanol and 5 ml of HCl (pH 0.3) for 24 hours. The mixture was stirred at room temperature, and the solvent was removed under a vacuum. The surfactin/surfactin monomethyl ester/surfactin dimethyl ester ratio obtained was about 0.1:2:1. The monomethyl esters were isolated by means of preparative RP HPLC using the same column as described in Example 2. The acetonitrile gradient in this case was between 35 and 50% B. Table 4 illustrates the isolated surfactin monomethyl esters.

TABLE 4

(In the following Table, the amino acid (AA) at position 4 is valine, and AA2 is leucine, unless otherwise stated)

| 14 | [Val7]- | 1008 | $C_{13}$ |
| 15 | [Leu7]- | 1022 | $C_{13}$ |
| | [Val7]- | 1008 | $C_{13}$ |
| 16 | [Leu7]- | 1022 | $C_{13}$ |
| | [Ile2, Val7]- | 1008 | $C_{13}$ |
| 18 | [Ile7]- | 1022 | $C_{13}$ |
| | [Val2, Val7]- | 1008 | $C_{14}$ |
| 19 | []Ile7- | 1022 | $C_{13}$ |
| 20 | [Val7]- | 1022 | $C_{14}$ |
| 21 | [Leu7]- | 1036 | $C_{14}$ |
| 22 | [Val7]- | 1022 | $C_{14}$ |
| | [Ile2, Val7]- | 1022 | $C_{14}$ |
| 23 | [Leu7]- | 1036 | $C_{14}$ |
| 24 | [Ile7]- | 1036 | $C_{14}$ |
| 25 | [Val7]- | 1036 | $C_{15}$ |
| | [Ile7]- | 1036 | $C_{14}$ |
| 26 | [Leu7]- | 1050 | $C_{15}$ |
| | [Val7]- | 1036 | $C_{15}$ |
| 27 | [Leu7]- | 1050 | $C_{15}$ |
| | [Ile2, Val7]- | 1036 | $C_{15}$ |
| 28 | [Ile7]- | 1050 | $C_{15}$ |
| 29 | [Ile7]- | 1050 | $C_{15}$ |
| 30 | [Ile2, Ile7]- | 1050 | $C_{15}$ |

EXAMPLE 4
Preparation of Dimethyl Esters of the Compounds of General Formula I The esterification of 100 mg of the surfactin mixture from Example 1 was performed within 48 hours using 5 ml of 37% HCl and 50 ml of methanol. The diesters were the major products, and they were isolated as described in Example 3. Table 5 illustrates the isolated surfactin dimethyl esters.

TABLE 5

| 34 | [Val7]- | 1022 | $C_{13}$ |
| 35 | [Leu7]- | 1036 | $C_{13}$ |
| 36 | [Ile7]- | 1036 | $C_{13}$ |
| 37 | [Val2, Val7]- | 1022 | $C_{14}$ |
| 38 | [Val7]- | 1036 | $C_{14}$ |
| 39 | [Leu7]- | 1050 | $C_{14}$ |
| 40 | [Ile7]- | 1050 | $C_{14}$ |
| | [Ile2, Val7]- | 1036 | $C_{14}$ |
| 41 | [Val7]- | 1050 | $C_{15}$ |
| 42 | [Leu7]- | 1064 | $C_{15}$ |
| 43 | [Ile7]- | 1064 | $C_{15}$ |
| | [Ile2, Val7]- | 1050 | $C_{15}$ |
| 44 | [Ile2, Ile7]- | 1064 | $C_{15}$ |

The $^1$H-NMR data of the diester of fraction 37 will be exemplified below, because this ester and the surfactin isoform which this ester is based upon is a new compound having the amino acid valine at position 2.

TABLE 6

| Amino acid | ppm | NH | $C_\alpha H$ | $C_\beta H$ | $C_\gamma H$ | $C_\delta H$ | |
|---|---|---|---|---|---|---|---|
| | | | [Val2, Val7] surfactin dimethyl ester (fraction 37) | | | | |
| L-Glu (1) | 8.82 | 5.01 | 2.51, | 2.39 | 2.71 | — | |
| L-Val (2) | 9.05 | 4.63 | | 2.43 | 1.20, | — | 0.91 |
| D-Leu (3) | 9.20 | 5.03 | 2.06, | 1.89 | 1.89 | 0.98, | |
| L-Val (4) | 8.75 | 4.79 | | 2.51 | 1.14 | — | |
| L-Asp (5) | 9.16 | 5.45 | 3.40, | 3.17 | — | — | |
| D-Leu (6) | 8.52 | 5.14 | | 1.97 | 1.97 | 0.98, | 0.91 |

TABLE 6-continued

| | | | | Chemical shift | | | |
|---|---|---|---|---|---|---|---|
| Amino acid | ppm | NH | $C_\alpha H$ | $C_\beta H$ | $C_\gamma H$ | | $C_\delta H$ |
| L-Val (7) | 9.03 | 4.91 | | 2.45 | 1.13, | | — |
| Fatty acid | | $^3$H 5.50 | $^2$H 2.93, 2.73 | | $^4$H 1.99, 1.85 | $^n$H 1.38, | 1.24 |

EXAMPLE 5
Determination of Antiviral Activity

To determine the antiviral activity of cyclic lipopeptides, herpes viruses were treated with the surfactin mixture from *Bacillus subtilis* (invariably referred to as surfactin hereinafter), and the number of infectious virus particles was determined as a function of time by seeding onto fresh host cells (final stage titration).

1. Herpes simplex virus type 1 (HSV-1) was taken up in 50 ml of Dulbecco's modified Eagle medium (ICN) including 5% (v/v) fetal calf serum (GIBCO) inactivated over 30 min at 56° C., and 80 μM of surfactin, sterile-filtered over a Nalgene syringe prefilter having a pore size of 0.1 μm. The initial titer was $5 \times 10^5$ $ID_{50}$/ml. By adding 1N HCl, the pH value of the inactivation batch was 7.8 constantly throughout the experiment, and the temperature was 22° C.
2. Aliquots were taken from the permanently stirred inactivation batch at intervals of 5, 10, 15, 30, 45, 60, 90, 120, and 180 minutes. Following a predilution of 1:10, these aliquots were used to produce a dilution series to the base 3. These dilutions were transferred to a 96-well flat-bottom microtiter plate (Nunc) into 8 parallel rows, each having 100 μl of each dilution stage. Each of the 96 wells of the microtiter plate had previously been charged with 100 μl of a Vero cell suspension at a cell density of $1.5 \times 10^5$ cells/ml.
3. The plates were incubated for 6 days at 37° C. and 5 vol.-% $CO_2$. The cells in the control batches with no virus dilution had grown to high densities. The cell cultures of the microtiter plate were examined using a light microscope. All those cultures indicating a cytopathogenic effect were rated as infected.
4. The titers were calculated as 50% infectious dose ($ID_{50}$) according to the method of Spearman and Kärbe [in: Biometrie. Grundzüge biologisch-medizinischer Statistic (1974), Ed.: L. Cavalli-Sforza, Gustav Fischer-Verlag, Stuttgart, pp. 171–173] and correlated to 1 ml of inactivation batch.

Within a period of 15 minutes, the initial titer dropped from $5.1 \times 10^5$ $ID_{50}$ to a residual infectiousness of 20$ID_{50}$. Following an incubation period of 30 minutes, the titer of infectious HSV-1 was 7 $ID_{50}$. After 60 minutes no infectious particles could be found anymore. Surfactin has a strong virucidal effect on herpes simplex virus, enabling an inactivation of 5 $\log_{10}$ HSV-1 particles in serum-containing culture medium within less than 60 minutes. Thus, compared to inactivation methods used so far, the number of enveloped infectious virus particles had decreased at a substantially higher rate when using surfactin.

EXAMPLE 6
Determination of the Activity Spectrum

To determine the antiviral activity spectrum of cyclic lipopeptides, viruses considered particularly resistant to physical and chemical methods of inactivation, among others, were treated with surfactin, and the remaining infectiousness of the virus particles was determined as a function of time.

1. The membrane-enveloped viruses listed in Table 1 were taken up in 50 ml of Dulbecco's modified Eagle medium (ICN) including 5% (v/v) fetal calf serum (GIBCO) freshly inactivated over 30 min at 56° C., and 80 μM of surfactin sterile-filtered over a Nalgene syringe prefilter having a pore size of 0.1 μm. The initial titers employed are illustrated in Table 1. By adding 1N HCl, the pH value of the inactivation batch was 7.8 constantly throughout the experiment, and the temperature was 22° C.

TABLE 1

Virus/cell systems used in the inactivation experiments

| Virus | Initial titer [$ID_{50}$/ml] | Host cell line | Model virus for |
|---|---|---|---|
| Porcine herpes virus (SHV-1) | $1.6 \times 10^5$ | Mink lung cells | human herpes viruses |
| Bovine herpes virus (BHV-1) | $4.3 \times 10^5$ | Bovine kidney cells | human herpes viruses |
| Herpes simplex virus type 2 (HSV-2) | $4.2 \times 10^4$ | Simian kidney cells | |
| Simian immuno-deficiency virus ($siv_{agm}$) | $1.6 \times 10^5$ | Human helper T cells | human immuno-deficiency viruses |
| Vesicular stomatitis virus (VSV) | $9.5 \times 10^6$ | Baby hamster fibroblasts | frequently used model virus |
| Semliki-Forest virus (SFV) | $7.0 \times 10^7$ | Baby hamster fibroblasts | western/eastern horse encephalitis |

2. Aliquots were taken from the permanently stirred inactivation batch at intervals of 5, 10, 15, 30, 45, 60, 90, 120, and 180 minutes. Following a predilution of 1:10, these aliquots were used to produce a dilution series to the base 3. These dilutions were transferred to a 96-well flat-bottom microtiter plate (Nunc) into 8 parallel rows, each having 100 μl of each dilution stage. According to the proliferation rate of the host cell, each of the 96 wells of the microtiter plate had previously been charged with 100 μl of the corresponding host cell suspension (Table 1) at cell densities of about $1.5 \times 10^5$–$5 \times 10^4$ cells/ml.
3. Depending on the particular cell line, the plates were incubated for 6-18 days at 37° C. and 5 vol.-% $CO_2$. The cells in the control batches with no virus dilution had grown to high densities. The cell cultures of the microtiter plate were examined using a light microscope. All those cultures indicating a cytopathogenic effect were rated as infected. As a result of insufficient light-microscopic evaluability, the cytopathogenic effect of $SIV_{agm}$ on the MOLT 4/8 human helper T cell line was determined according to the description of the cell proliferation-dependent test according to Mosman [J. Immunol. Meth. 65, 55–63, 1983] using the MTT dye.
4. The titers were calculated according to the description in Example 1, section 5.

All of the above-listed enveloped viruses could be inactivated by using surfactin in a serum-containing medium. After 120 minutes, less than 0.02% of the employed SHV-1, BHV-1, and HSV-2 infectiousness could be detected. With the viruses VSV and $SIV_{agm}$, such a ratio of residual infectiousness was reached after an incubation period of only 60 minutes. The surfactin lipopeptide acts directly on a variety of lipid-enveloped viruses at a high inactivation rate.

EXAMPLE 7

Effect of Lipopeptide Concentration

The effect of the concentration of cyclic lipopeptide on the inactivation efficiency may be quantified by determining the inactivation rate (decrease of virus infectiousness per inactivation time).

1. Porcine herpes virus (SHV-1) was taken up in 25 ml of Dulbecco's modified Eagle medium (ICN) including 5% (v/v) fetal calf serum (GIBCO) inactivated over 30 min at 56° C., and surfactin concentrations of 0, 10, 20, 30, 40, 50, 60, 70, 75, 80, 90, and 100 μM, respectively. To this end, the surfactin was dissolved in culture medium and sterile-filtered over a syringe prefilter (Nalgene, pore size 0.1 μm). The initial titer was $2\times10^4$ $ID_{50}$/ml. The temperature in the permanently stirred inactivation batch was 22° C., and the pH value was 7.8.
2. Following addition of surfactin, aliquots were taken from the inactivation batch at intervals of 2, 5, 10, 15, and 20 minutes and immediately subjected to a 1:10 predilution in medium.
3. Using these predilutions, a dilution series to the base 3 was produced. The dilutions were transferred to a 96-well flat-bottom microtiter plate (Nunc) into 8 parallel rows, each having 100 μl of each dilution stage. Each of the 96 wells of the microtiter plate had previously been charged with 100 μl of a mink lung cell suspension at a cell density of about $1.0\times10^5$ cells/ml.
4. The incubation of the cell cultures in the microtiter plates, the evaluation of these microtiter plates, and the calculation of the titer of remaining infectious virus at the respective times of withdrawal were carried out according to the description in Example 1, sections 4 and 5.

The inactivation rate increases exponentially with the lipopeptide concentration. Within a lipopeptide concentration range of from 10 to 80 μM surfactin, the inactivation rate increased from 0.19 to 0.6 $\log_{10}$ $D_{50}$/10 min. At a surfactin concentration of 100 μM, the employed infectious SHV-1 particles were inactivated at a rate of 1.41 $\log_{10}$ $ID_{50}$/10 min. The surfactin lipopeptide permits inactivation of lipid-enveloped viruses within a broad concentration range. The lipopeptide concentration may be selected according to product properties and process profile.

EXAMPLE 8

Virus Inactivation at Various Reaction Temperatures

The effect of temperature on the virus inactivation during the inactivation reaction may be quantified by determining the inactivation rate (decrease of virus infectiousness per inactivation time).

1. Porcine herpes virus (SHV-1) was taken up in 25 ml of Dulbecco's modified Eagle medium (ICN) including 5% (v/v) fetal calf serum (GIBCO) inactivated over 30 min at 56° C. and surfactin at a concentration of 80 μM. The surfactin was dissolved in culture medium and sterilized-filtered over a syringe prefilter (Nalgene, pore size 0.1 μm). The initial titer was $1\times10^5$ $ID_{50}$/ml. By adding 1N HCl, the pH value of the inactivation batch was 7.8 constantly throughout the experiment. The respective inactivation batches were adjusted to 5, 10, 15, 20, 25, and 30° C. with an accuracy of ±0.01° C. in a water bath [Grant, model W14-ZD/CZ1] and stirred permanently.
2. Following surfactin addition, aliquots were sampled at intervals of 2, 5, 10, 15, and 20 minutes and immediately subjected to a 1:10 predilution in medium.
3. Using these predilutions, a dilution series to the base 3 was produced. The dilutions were transferred to a 96-well flat-bottom microtiter plate (Nunc) into 8 parallel rows, each having 100 μl of each dilution stage. Each of the 96 wells of the microtiter plate had previously been charged with 100 μl of a mink lung cell suspension at a cell density of about $1.0\times10^5$ cells/ml.
4. The incubation of the cell cultures in the microtiter plates, the evaluation of these microtiter plates, and the calculation of the titer of remaining infectious virus at the respective times of withdrawal were carried out according to the description in Example 1, sections 4 and 5.

Within the tested temperature range of from 5 to 30° C., there was significant inactivation of SHV-1 in the serum-containing culture medium. The inactivation rate increased linearly from 0.05 at 5° C., via 0.25 at 20° C., and to 0.45 $\log_{10}$ $ID_{50}$/min at 30° C. The surfactin lipopeptide permits treatment of heat-labile products in order to inactivate lipid-enveloped viruses, as well as time-saving, rapid inactivation at high temperatures.

EXAMPLE 9

Determination of Cytotoxicity of Surfactin on Adherent Cells

The cytotoxic effect of cyclic lipopeptides on adherent cells in a culture was determined according to a modification of the crystal violet test by D. A. Flick and G. E. Gifford [J. Immunol. Meth. 68, 167–175, 1984].

1. Cells of the lines ML (mink lung cells), CV1 (green guenon kidney cells), $Hep_2$ (human epithelial cells), CRFK (cat kidney cells), and BHK21 (hamster kidney cells) freshly treated with trypsin were taken up in Dulbecco's modified Eagle medium (ICN) including 5% (v/v) fetal calf serum (GIBCO) freshly inactivated over 30 min at 56° C., and 100 μl of cell suspension (about $1–2\times10^5$ cells/ml) was pipetted into each well of a 96-well flat-bottom culture plate (Nunc). The culture was incubated for 3 hours at 37° C. in the presence of 5 vol.-% $CO_2$.
2. Surfactin dissolved in culture medium was sterile-filtered (Nalgene syringe prefilter, pore size 0.1 μm and diluted to various concentrations using fresh culture medium. 50 μl of the nutrient medium including various concentrations of surfactin was added to the grown cells. The culture plate was incubated for another 2 days at 37° C. and in the presence of 5 vol.-% $CO_2$.
3. After 3 days, the cells of the lines ML, $Hep_2$, and BHK21, and after 8 days, the cells of the lines CV1 and CRFK had grown to high cell densities, forming homogeneous cell lawns. The medium supernatant was discarded, and 50 μl of crystal violet solution was pipetted into each batch. The crystal violet solution was composed of 3.75 g of crystal violet, 1.75 g of NaCl, 161.5 ml of absolute ethanol, 43.2 ml of 37% formaldehyde (all chemicals supplied by Merck) ad 500 ml of deionized and distilled water. After 20 min, the crystal violet solution was thoroughly washed out of the cavities using deionized water, and the microtiter plate was air-dried.
4. The remaining cell-bound dye was dissolved by adding 100 μl of a solution of 50% absolute ethanol, 0.1% of glacial acetic acid, 49.9% of deionized and distilled water per cavity and dispersed homogeneously at by intense agitation for 5 minutes. The photometric determination of the color intensity which is in linear relationship to the cell density, was effected at 550 nm (EAR 400 AT, SLT-Labinstruments). The concentration resulting in a 50% reduction of the cell number was determined.

A cytotoxic effect of 50% at a medium concentration of 48 μM for the $Hep_2$, 37 μM for the BHK21, 45 μM for the CRFK, and 43 µM for the ML cells was determined with surfactin. The CRFK and Hep$_2$ cells did not exhibit any changes in cellular growth at surfactin concentrations of up to 30 µM. With ML and BHK21 cells, a reduction in growth by about 15% was observed at such a surfactin concentration. In long-term examinations, a surfactin concentration of 40 µM as used in Example 1 resulted in a cell density reduction to 15% for the CRFK and Hep$_2$ cells, to 45% for the ML cells, and to 57% for the BHK21 cells compared to non-treated control batches. None of the tested cultures tolerated surfactin concentrations higher than 65 µM. All of the tested cell cultures tolerated the presence of the surfactin lipopeptide over the short period of time required for the inactivation of lipid-enveloped viruses.

EXAMPLE 10
Biotechnological Application
Inactivation of Enveloped Viruses in Cell Cultures Using genetic engineering, any cell line will be capable of producing potentially valuable substances such as interferons, growth factors, etc.. Circumstantially, such cell cultures may be contaminated by various virus species. Therefore, virus contaminations should be removed at such an early stage as the starting cell culture. The elimination of a herpes virus from a mink lung cell culture will now be described as an example. Porcine herpes virus type 1 (SHV-1) induces a distinct cytopathogenic effect, the absence thereof being a direct evidence for the success of inactivation.

1. In a Petri dish (Ø 10 cm, Nunc), about 1×10$^4$ ML cells (mink lung cells) freshly treated with trypsin were subjected to a passage using Dulbecco's modified Eagle medium (ICN) including 5% (v/v) fetal calf serum (GIBCO) inactivated over 30 min at 56° C. The cell culture medium was removed from the grown cells which were infected with about 100 TCID$_{50}$ of SHV-1. Following a one hour incubation, the inoculum was removed and the cell lawn was covered with a layer of 10 ml of Dulbecco's modified Eagle medium (ICN) including 5% (v/v) fetal calf serum (GIBCO) and 50 µM of surfactin. To this end, the surfactin was dissolved in PBS at a concentration of 1 mM and autoclaved (23 min at 123° C.).
2. The ML cell culture was incubated for 3 days at 37° C. and 5 vol.-% CO$_2$. The cells covered 30% of the Petri dish bottom, and their removal was possible using 0.25% trypsin, 2 µM EDTA. In a Petri dish (φ 10 cm, Nunc), all the cells were subjected to a further passage with Dulbecco's modified Eagle medium (ICN) including 5% (v/v) fetal calf serum (GIBCO) inactivated over 30 min at 56° C., and 40 µM surfactin. The treatment was repeated twice.
3. Subsequent to ten passages with no surfactin, 1 ml of cell culture supernatant was placed on a fresh ML culture which, following 7 days of incubation, was then examined for a virus-related cytopathogenic effect (CPE) using a light microscope.

No cytopathogenic effect as an indication of virus growth could be observed in the ML cell cultures.

EXAMPLE 11
Product Safety
Inactivation of SIV in an Albumin Solution

Serum contains a variety of economically and medically important components such as hormones, immunoglobulins, coagulation factors, enzymes, cholesterols, lipoproteins, albumins, etc.. A serum may be fractionated using organic solvents such as ethanol, ether, polyethylene glycol at low temperatures, and by precipitation using salt or a pH change, thus purifying the components. However, viruses occurring in blood, such as the HIV retrovirus may be present in the purified blood product as infectious particles. As an example of a virus inactivation to follow necessarily, bovine serum albumin (BSA) was treated with surfactin. To demonstrate the efficacy, albumin was added with a dose of simian immunodeficiency virus (SIV) not encountered under natural conditions, and the number of infectious virus particles was determined as a function of time by seeding onto fresh host cells (final stage titration).

1. Simian immunodeficiency virus (SIV) was taken up in 50 ml of PBS including 50 mg/ml BSA and 80 µM surfactin (dissolved in PBS at a concentration of 1 mM and autoclaved). The initial titer was 1.6×10$^5$ TCID$_{50}$/ml. By adding 1N HCl, the pH value of the inactivation batch was 7.8 constantly throughout the experiment, and the temperature was 22° C.
2. Aliquots were taken from the permanently stirred inactivation batch at intervals of 5, 10, 15, 30, 45, 60, 90, 120, and 180 minutes. Following a predilution of 1:10, these aliquots were used to produce a dilution series to the base 3. These dilutions were transferred on a 96-well flat-bottom microtiter plate (Nunc) into 8 parallel rows, each having 100 µl of each dilution stage. Each of the 96 wells of the microtiter plate had previously been charged with 100 µl of a Molt4, Klon 8 cell suspension at a cell density of 5×10$^4$ cells/ml.
3. The plates were incubated for 14 days at 37° C. and 5 vol.-% CO$_2$. The cells in the control batches with no virus dilution had grown to high densities. The cell cultures of the microtiter plate were examined using a light microscope. All those cultures indicating a cytopathogenic effect were rated as infected.
4. The titers were calculated as 50% infectious dose (TCID$_{50}$) according to the method of Spearman and K ärbe [in: Biometrie. Grundzüge biologisch-medizinischer Statistik (1974), Ed.: L. Cavalli-Sforza, Gustav Fischer-Verlag, Stuttgart, pp. 171–173] and correlated to 1 ml of inactivation batch.

Within a period of 15 minutes, the initial titer dropped from 1.6×10$^5$ TCID$_{50}$ to a residual infectiousness of 1.5×10$^3$ TCID$_{50}$. After an incubation period of 60 minutes, the titer of infectious SIV was 7 TCID$_{50}$. After 120 minutes, no infectious particles could be found anymore.

EXAMPLE 12
Product Safety
Combined use of Surfactin and Moist Heat for Inactivating SIV in an Albumin Solution Once isolated and purified, products obtained by blood and biotechnology are frequently subjected to a heat treatment (pasteurization). Such a heat treatment may be combined with an SD process. Owing to its thermal stability, surfactin may also be used in combination with a heat inactivation procedure. The example describes the inactivation of simian immunodeficiency virus (SIV) in serum albumin in order to demonstrate the synergistic effect of heat and surfactin on the virus inactivation.

1. Simian immunodeficiency virus (SIV) was taken up in 50 ml of PBS including 50 mg/ml BSA and 80 µM surfactin (dissolved in PBS at a concentration of 1 mM and autoclaved). The initial titer was 1.6×10$^5$ TCID$_{50}$/ml. By adding 1N HCl, the pH value of the inactivation batch was 7.8 constantly throughout the experiment. Prior to adding the virus suspension, the batch had been preheated to 60° C. on a water bath and held constant during the experiment.
2. Aliquots were taken from the permanently stirred inactivation batch at intervals of 2, 5, 10, 15, 30, 45, and 60 minutes. Following a predilution of 1:10, these aliquots were used to produce a dilution series to the base 3. These dilutions were transferred to a 96-well flat-bottom microtiter plate (Nunc) into 8 parallel rows, each having 100 $\mu$l of each dilution stage. Each of the 96 wells of the microtiter plate had previously been charged with 100 $\mu$l of a Molt4, Klon 8 cell suspension at a cell density of $5\times10^4$ cells/ml.

3. The plates were incubated for 14 days at 37° C. and 5 vol.-% $CO_2$. The cells in the control batches with no virus dilution had grown to high densities. The cell cultures of the microtiter plate were examined using a light microscope. All those cultures indicating a cytopathogenic effect were rated as infected.
4. The titers were calculated as 50% infectious dose ($TCID_{50}$) according to the method of Spearman and K ärbe [in: Biometrie. Grundzüge biologisch-medizinischer Statistik (1974), Ed.: L. Cavalli-Sforza, Gustav Fischer-Verlag, Stuttgart, pp. 171–173] and correlated to 1 ml of inactivation batch.

Within a period of 5 minutes, the initial titer dropped from $1.6\times10^5$ $TCID_{50}$ to a residual infectiousness of $9.3\times10^2$ $TCID_{50}$. After 20 minutes of incubation, no infectious particles could be found anymore. When using the combined heat/surfactin procedure, the infectiousness of introduced SIV was inactivated more rapidly by a factor of at least 10 compared to an equal surfactin concentration at room temperature or by heat treatment with no antiviral additives.

EXAMPLE 13

Maximum Inactivation Rates

The maximum attainable inactivation rates were determined for three virus families. The inactivation conditions were: pH 7.8; 80 $\mu$M surfactin; aqueous medium including 5% fetal calf serum; stirring; 22° C.

| | Drop in infectiousness [$\log_{10}$ $TCID_{50}$#] | | | |
|---|---|---|---|---|
| Virus | after 5 min | after 30 min | after 60 min | after 120 min |
| Herpes viruses | 2.30 | 4.90 | 5.40 | — |
| Retroviruses | 1.30 | 2.90 | 4.40 | — |
| Rhabdoviruses | 1.00 | 3.60 | 4.50 | 5.40 |

Dose infecting 50% of tissue culture

What is claimed is:

1. A method of inactivating substantially all lipid-enveloped viruses in a composition comprising at least one isolated protein, which comprises contacting said composition with a cyclic lipoheptapeptide of the following formula (I)

(I)

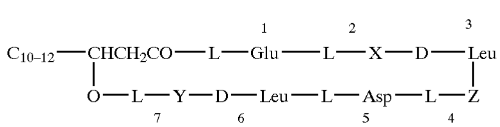

a salt, ester or mixture thereof in an amount and for a time up to 2 hours and at a temperature effective to inactivate substantially all lipid-enveloped viruses in the composition, wherein in the formula (I), X and Y each independently represent the amino acids Leu, Ile or Val, Z represents the amino acids Val or Ala, and $C_{10-12}$ represents a linear or branched, saturated alkyl group.

2. The method according to claim 1, characterized in that the cyclic lipopeptide is a naturally characterized in that the cyclic lipopeptide is a naturally occurring lipopeptide, or is a chemically synthesized lipopeptide, or is a lipopeptide produced or modified by genetic engineering.

3. The method according to claim 1, characterized in that $C_{10-12}$ is a $C_{11}$ alkyl or $C_{12}$ alkyl.

4. The method according to claim 1, characterized in that compounds of general formula I are used, wherein X and Y represent Leu, and Z represents Val.

5. The method according to claim 1, characterized in that compounds of general formula I are used, wherein X represents Ile or Val.

6. The method according to claim 1, characterized in that lipid-enveloped human and non-human and animal viruses are inactivated.

7. The method of claim 1, wherein said at least one isolated protein is selected from the group consisting of vaccines, monoclonal antibodies, hormones and recombinant proteins.

8. A method of inactivating substantially all lipid-enveloped viruses in a composition comprising at least one isolated protein which comprises contacting said composition with a cyclic lipoheptapeptide of the following formula (I)

(I)

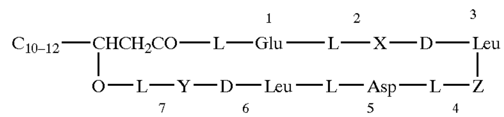

a salt, ester or mixture thereof, at temperatures higher than room temperature, for a period of 5–30 min and in an amount effective to inactivate substantially all lipid-enveloped viruses in the composition, wherein in the formula (I), X and Y each independently represent the amino acids Leu, Ile or Val, Z represents the amino acids Val or Ala, and $C_{10-12}$ represents a linear or branched, saturated alkyl group.

9. The method of claim 8, wherein the temperature is 30–60° C.

10. The method according to claim 1, characterized in that esters of the compound of general formula I are used.

11. The method of claim 10, wherein the esters are monoesters.

12. The method according to claim 1, characterized in that one or more viruses selected from the group consisting of herpes viruses, immunodeficiency viruses, vesicular stomatitis virus (VSV), and Semliki-Forest virus (SFV) are inactivated.

13. The method of claim 12, wherein the herpes virus is herpes simplex virus type 1 (HSV-1), herpes simplex virus type 2 (HSV-2), bovine herpes virus type 1 (BHV-1) or suid herpes virus type 1 (SHV-1).

14. Isolated lipoheptapeptides of general formula I (I)

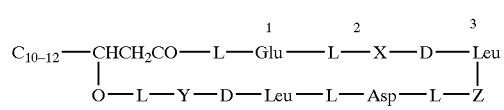

and the salts and esters thereof, in which formula I X and Y independently represent Val or Ile, and Z represents Val.

* * * * *